United States Patent [19]
Bylander

[11] Patent Number: 5,654,786
[45] Date of Patent: Aug. 5, 1997

[54] OPTICAL LENS STRUCTURE AND CONTROL SYSTEM FOR MAINTAINING A SELECTED CONSTANT LEVEL OF TRANSMITTED LIGHT AT A WEARER'S EYES

[75] Inventor: E. Gerald Bylander, Sherman, Tex.

[73] Assignee: Robert C. Burlingame, Sherman, Tex.

[21] Appl. No.: 584,567

[22] Filed: Jan. 11, 1996

[51] Int. Cl.⁶ .............................. G02C 7/12; G02C 1/00
[52] U.S. Cl. .............................. 351/49; 351/41; 351/158
[58] Field of Search .............................. 351/49, 158, 41, 351/44, 45, 46; 359/62, 63

[56] References Cited

U.S. PATENT DOCUMENTS

| | | | |
|---|---|---|---|
| 3,245,315 | 4/1966 | Marks et al. | 88/61 |
| 3,531,182 | 9/1970 | Land et al. | 350/150 |
| 3,663,088 | 5/1972 | Maldonado et al. | 350/150 |
| 4,201,450 | 5/1980 | Trapani | 351/49 |
| 4,264,154 | 4/1981 | Petersen | 351/49 |
| 4,529,873 | 7/1985 | Ballmer et al. | 250/201 |
| 4,572,619 | 2/1986 | Reininger et al. | 350/392 |
| 4,968,127 | 11/1990 | Russell et al. | 351/49 |
| 5,015,086 | 5/1991 | Okaue et al. | 351/44 |

*Primary Examiner*—Hung X. Dang
*Attorney, Agent, or Firm*—Harris, Tucker & Hardin, P.C.

[57] ABSTRACT

A lens structure and electronic control system is provided for use in eyeglasses. The lens structure is formed by a pair of lenses with a transmission layer formed by an electro-optic material is disposed therebetween. The transmission layer is used to control the amount of light that is transmitted through the lens structure by placement of a variable voltage placed across it. The transmission layer can be formed by either a dichroic dye or by a ferro-electric material such as PLZT. The electronic control system uses a photoamperic sensor placed behind the lens structure to develop a current proportional to the transmitted light. The current is converted into a voltage which is compared to a desired transmission range. If the sensed transmission level is outside the desired range the control circuit causes a power supply to add or decrease the charge across the lens as necessary to bring the transmitted light level back into the desired range. The use of a ferro-electric material also requires the use of a high voltage power supply to provide the necessary voltages to operate the lens structure.

24 Claims, 3 Drawing Sheets

OPTICAL LENS STRUCTURE AND CONTROL SYSTEM FOR MAINTAINING A SELECTED CONSTANT LEVEL OF TRANSMITTED LIGHT AT A WEARER'S EYES

FIELD OF THE INVENTION

The present invention relates to lens structures which have an optical transmissivity that can be electronically controlled, and more specifically where the optical transmissivity is maintained at or within a preset level. The present invention also relates to eyewear incorporating an electronically controlled lens structure.

BACKGROUND OF THE INVENTION

The are many instances when it is desirable or necessary to control the amount of light passing through lens or lens structure. One of these instances relates to the lenses used in eyewear. Continuous control of optical transmissivity across a broad range of magnitudes is particularly desirable in many medical applications such as diagnosis and treatment of retinal disease, visual field abnormalities known a scotomas, optic neuropathy, macular degeneration, and the like. Diagnosis of these conditions can be problematic using uncontrolled ambient light since the magnitude of the symptoms of these diseases can vary with ambient light levels.

For patients suffering from retinal diseases, sudden changes in ambient light levels, such as emerging from a dimly lit room into a bright sunny day, and vise versa, can cause serious problems and momentary blindness. It would be desirable to maintain these patients in a partially dark adapted state. This partially dark adapted state would involve maintaining a constant light level at the patients eyes despite variations in ambient light levels.

Existing devices for controlling optical transmissivity are not suited for the applications described. Many of these devices cannot continuously control transmissivity over a broad range of ambient light levels. An example of this type of device is a flash blindness device that darkens only when a sudden change in ambient light levels is detected. One such device is disclosed in U.S. Pat. No. 3,245,315 to Marks et al.

Other devices that control optical transmissivity have their transmissivity dependent on ambient light levels. These devices locate their sensors to detect the ambient light levels and not the transmitted light levels. Transmitted light through these devices is not constant and is dependant on the ambient light levels. Ideally, for the applications described, transmitted light should be independent of ambient light levels and constant within a narrow range. Examples of devices with transmitted light levels dependant on ambient light levels are U.S. Pat. No. 5,015,086 to Okaue et al. and U.S. Pat. No. 4,968,127 to Russell et al.

What is needed is a device to continuously control optical transmissivity over a broad range wherein the transmitted light is independent of ambient light levels.

SUMMARY OF THE INVENTION

It is, therefore, an object of the invention to provide a lens structure and control system for eyewear that provides a high degree of control over the amount of light passing through the lens.

It is another object of the invention to provide a lens structure for eyewear where the optical transmissivity is continuously controllable over a broad range of transmission levels.

It is yet another object of the invention to provide a lens structure for eyewear where the transmitted light level is independent of ambient light levels.

It is another object of the invention to provide a lens structure that changes optical transmissivity in response to a change in ambient light levels faster than the recognition level of the wearer.

In one embodiment of the invention the lens structure is comprised of a transmission layer which is a ferro-electric material, preferably PLZT, but can be lithium niobate or tantalate. The transmission layer is placed between two polarizing lenses. A high voltage power supply is used to develop a voltage across the transmission layer which rotates the plane of polarization of the light passing through it in an amount relative to the voltage across the PLZT. This structure controls the amount of light passing through the lens structure by controlling how much light is passed by the second polarizer.

For example, if the two polarizers are aligned with the planes of polarization at right angles to each other almost no light would normally be allowed to pass through the lens structure. However, if a particular large voltage is developed across the transmission layer the polarized light passing through the first polarizer is rotated, for example, 90° such that it lies in the same plane as the second polarizer and would pass undiminished through the second polarizer. A lesser voltage across the transmission layer would rotate the polarized light less than 90° causing less than total amount of light passed through the first polarizer to pass through the second polarizer.

The amount of light passing through the lens is controlled by a control circuit that begins with a sensor that measures the amount of light passing through the lens and develops a current proportional to that amount of light. The current is converted to a voltage and sent to a window comparator configuration where the sensed voltage level is compared to an upper threshold and a lower threshold. If the sensed voltage is between the two thresholds the control circuit takes no action. However, if the sensed voltage is below the lower threshold or above the upper threshold the control circuit turns on the high voltage power supply to increase the voltage across the transmission layer or shorts the transmission layer electrodes together to bleed off charge, respectively.

In an alternate embodiment the PLZT and dual polarizer structure is replaced by a transmission layer formed by liquid dichroic dye between two lenses one of which can incorporate a polarizer if the application warrants. The dichroic dye lightens, or increases the amount of light passing through it, in response to a voltage developed across the dye. The dichroic dye lens structure can be controlled by the control circuit described above except that the dichroic dye does not require the very high voltages required by the PLZT lens structure.

BRIEF DESCRIPTION OF THE DRAWINGS

Other objects and features of the invention will become more readily apparent from the following detailed description when read in conjunction with the accompanying drawings, wherein.

DETAILED DESCRIPTION

Figure 1:
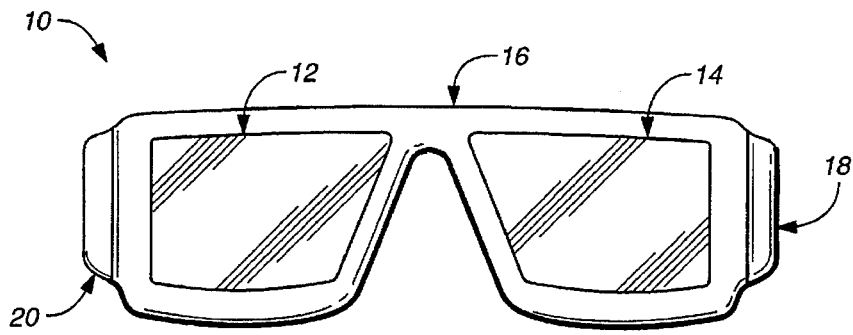
FIG. 1 is a frontal view of eye glasses incorporating the lens structure and electrical control system of the present invention.
Figure 2:
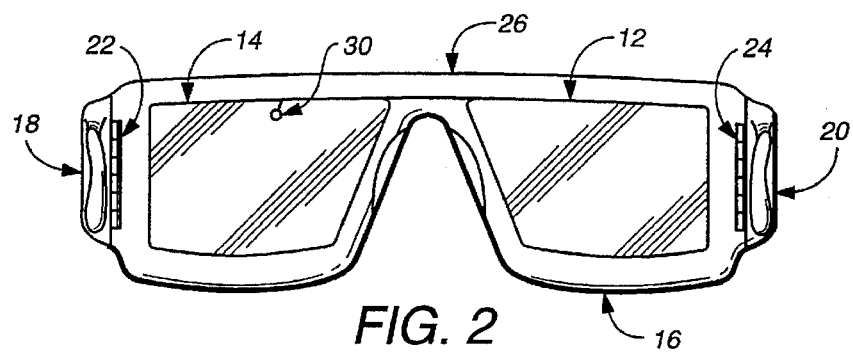
FIG. 2 is a rear view of the eye glasses shown in FIG. 1.
Figure 3:
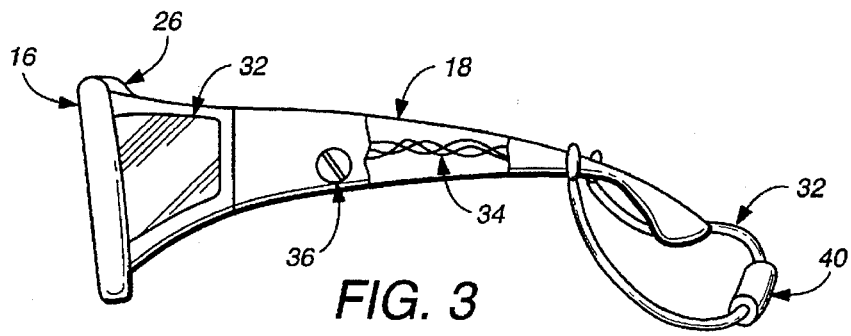
FIG. 3 is a side view of the eye glasses shown in FIG. 1.

FIG. 1, 2 and 3 show eyewear 10 incorporating the invention. FIG. 1 is a frontal view of eyewear 10 which includes lenses 12 and 14 mounted in frame 16. Lenses 12 and 14 shown in FIG. 1 are individually formed by two lenses with transmission layer formed by a liquid dichroic dye sealed in between. Dichroic dye, as configured in the present invention, responds by lightening when in the presence of an electric field. The amount of the increase in transmissivity by the dichroic dye is proportional to the amount of electric field allowing the invention to continuously vary the optical transmissivity of the lens in response to varying ambient light conditions. The electric field is developed across the transmission layer of dichroic dye by opposing electrodes formed by continuous layers of indium tin oxide film which coat the interior surfaces of the two lenses. The layers of indium tin oxide are transparent and connected to opposite poles of a power supply to be described with reference to FIG. 9.

FIG. 2 is a rear view of eyewear 10 and shows ear pieces 18 and 20 held to frame 16 by hinges 22 and 24. Hinges 22 and 24 allow ear pieces 18 and 20 to fold in toward frame 16 for storage of eyewear 10, as is known in the art. Also shown is sensor 30 which is mounted to the rear of lens 14 and measures the amount of light that passes through lens. Sensor 30 is a photovoltaic detector and produces a current proportional to the amount of light detected. The preferred embodiment of the invention uses a Gallium Arsenide Phosphide (GaAsP) green or red light emitting diode (LED) connected as a photoamperic cell to function as sensor 30. The photoamperic cell is connected to lens 14 using a transparent non-yellowing and stress free epoxy such as Tra-Bond brand epoxy from Tra-Con of Medford, Mass. A silicon photoamperic cell can be used with the dichroic dye and non-polarizing lenses, but GaAsP is preferred for the PLZT and dichroic dye using polarizers due to its lack of detection in the infra-red spectrum. Detection by sensor 30 of light outside the visible spectrum can cause serious discrepancies between the sensed light level and the actual visible light level and should be avoided.

Additionally, care must be taken to prevent light from reaching sensor 30 from any direction other than through lens 14. To this end, eyewear 10 includes seal 26 attached to the top of frame 16. Seal 26 is formed from a pliant material such as foam rubber or a thin plastic membrane and extends from frame 16 to the forehead of the wearer preventing light from reaching sensor 30 through the space between frame 16 and the wearer.

FIG. 3 shows a side view of eyewear 10. Ear piece 18 is formed to prevent light from reaching sensor 30 from the side of eyewear 10 for the same reason as seal 26. Ear piece 18 includes peripheral lens 32 which is polarized to restrict the amount of light that can enter peripheral lens 32. Peripheral lens is included to allow the wearer peripheral vision which is critical in applications such as driving. The electronic control circuitry and power supply circuitry are housed in ear pieces 18 and 20. Wiring connections 34 show the wiring of the circuitry discussed with reference to FIGS. 6 to 9.

Figure 6:
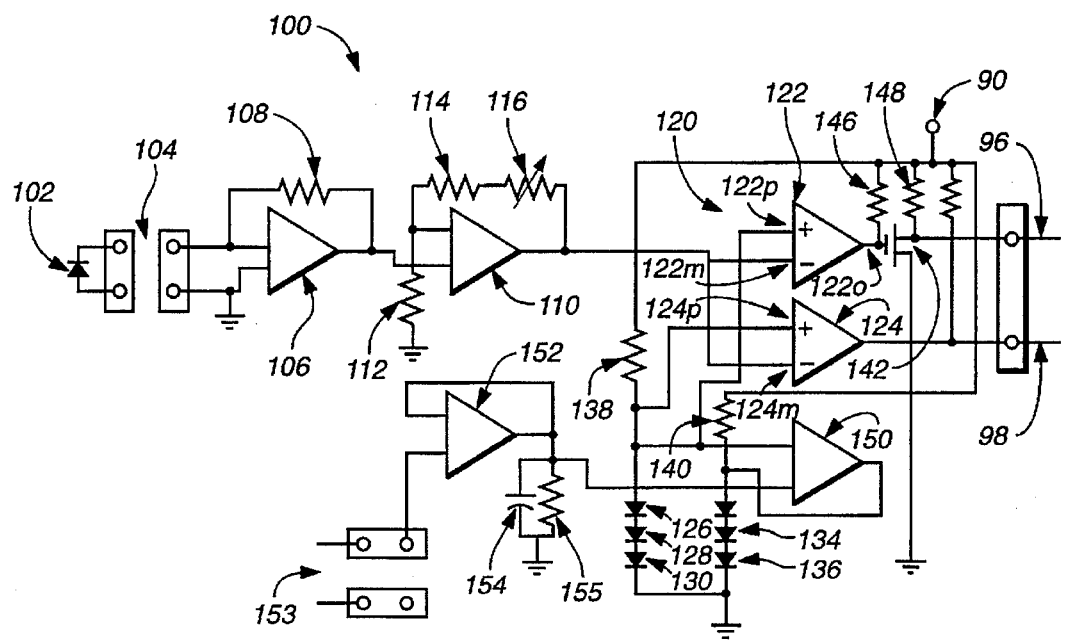
FIG. 6 is a schematic diagram of the preferred embodiment of the control circuit.

Dial 36 allows the user to set the desired transmission level by controlling resistor 116 from FIG. 6 and can act as an on/off switch. An alternate on/off switch can be mounted in earpiece 18 such that when ear piece 18 is folded out from the storage position using hinge 22 contact by ear piece 18 to frame 16 activates the switch turning on the electronics of the invention. Additionally, eyewear 10 is shown in FIG. 3 with neckstrap 38. Neckstrap 38 can be configured to house lithium cell 264 from FIG. 9 in cell housing 40. Without neckstrap 38 the lithium cell for the electronics can be housed in ear piece 18.

Figure 4:
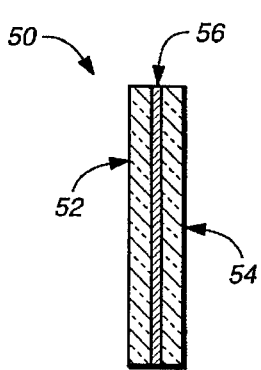
FIG. 4 is a side view of the ferro-electric lens structure.

FIG. 4 shows another embodiment of lenses 12 and 14. Lens structure 50 is formed by polarizers 52 and 54 separated by a ferro-electric material 56 which is preferably a lead-lanthanum zirconate/titanate of the quaternary $(Pb_{1-x}La_x)(Zr_yTi_z)_{1-x/4}O_3$, system, commonly known as PLZT. PLZT rotates the plane of polarization of an electromagnetic wave passing through it in response to an electric field. The amount of rotation of the electro-magnetic wave is proportional to the magnitude of the electrical field placed on the PLZT.

Lens structure 50 uses polarizer 52 to polarize the light entering ferro-electric material 56 and the second polarizer, referred to as analyzer 54 to polarize the light exiling ferro-electric material 56. An electric field is induced in ferro-electric material 56 such that the light passed by polarizer 52 is rotated by ferro-electric material 56 and a percentage of the remaining light is absorbed by analyzer 54. Since the amount of rotation is proportional to the electric field the amount of light passing through lens structure can be controlled by controlling the electric field.

Polarizer 52 and analyzer 54 of lens structure 50 can be oriented in two ways. By orienting the polarizers in the same plane the lens structure is transparent when no electric field is applied to ferro-electric material 56. One advantage of this arrangement is that it is transparent if the power supply or control circuit fail. Alternatively, if polarizer 52 and analyzer 54 are oriented perpendicularly, the lens structure is opaque when no electric field is applied to ferro-electric material 56.

Figure 5:
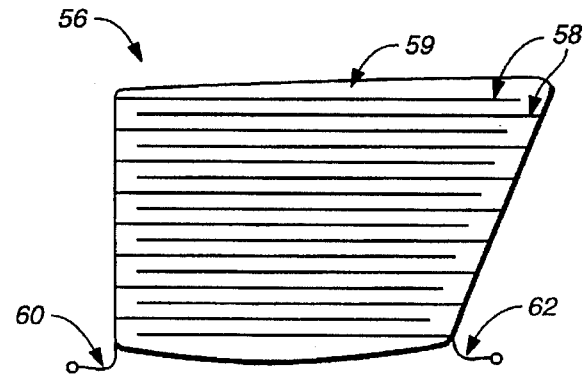
FIG. 5 is a frontal view of the ferro electric material.

FIG. 5 is a frontal view of ferro-electric material 56 used in the present invention. The PLZT used as ferro-electric material 56 in the preferred embodiment is not capable of developing a suitable electric field across the entire lens. As a result ferro-electric material 56 is constructed with small filaments 58 on surface 59 of ferro-electric material extending in alternating succession from either side of ferro-electric material 56. Filaments 58 extending into ferro-electric material 56 from opposite sides are given opposite electrical charges by the power supply of the present invention. Filaments 58 allow the electric field to be formed between each of oppositely charged filaments 58. If filaments 58 are placed on both surface 59 and the opposing surface (not shown), of ferro-electric material 56, an electric field can be formed between oppositely charged filaments on opposing surfaces. Filaments 58 are connected to the high voltage power supply using electrical connections 60 and 62.

Since dichroic dye lenses 14 and 12 shown in FIG. 1 does not require polarizers, it may have a range of transmissivity from 10 to 80%. In contrast, lens structure 50 of FIG. 4 by requiring polarizers can have a transmissivity that normally ranges from 4 to 24%, but can be as great as $1\times10^{-3}$ to 36%. If the application requires, such as sunglasses for a fisherman where the light reflected off the water is polarized in a single plane, a polarizer can be added to the dichroic dye lens resulting in a range of transmissivity from 4 to 32%.

FIG. 6 is a circuit diagram of control circuit 100, the preferred embodiment of the control circuit for the present invention which is configured to control perpendicularly oriented polarizers. The control circuit can easily be adapted to accommodate parallel polarizers by reversing the comparator wiring of window comparator 120 described below. Photo diode 102 acts as sensor 30 from FIG. 1. Photo diode 102 is preferably made from gallium arsenide phosphide (GaAsP) or silicon, but must be excited almost exclusively by light in the visible spectrum. Photo diodes sensitive to infra-red light, such as unfiltered silicon, can cause a serious degradation in system performance since commercial visible polarizers are ineffective in the infra-red. As described above, photo diode 102 is mounted behind the lens structure such that it measures only the light passing through the lens.

Photo diode 102 is effectively short circuited by connecting to op-amp 106 so that it generates a current proportional to the incident light intensity that is then passed through connector 104 to op-amp 106 which, in conjunction with resistor 108 converts the current developed by photo diode 102 to a voltage that can be used by the rest of control circuit 100. Op-amp 110 is used with resistors 112, 114 and variable resistor 116 to amplify the signal from photo diode to a level relative to the desired light level and the preset reference voltages.

Window comparator circuit 120 utilizes discrete comparators 122 and 124 to compare the signal representing the light received by the sensor to a high reference voltage and a low reference voltage. The lens structure, as discussed above with reference to FIGS. 4 and 5, is opaque when there is no voltage developed across it and becomes progressively more transparent as the voltage across the lens structure is increased from the threshold until the lens reduces to its desired transparency to maintain the transmitted light at the predetermined level. Therefore, the high reference voltage is used to determine when the correct amount of light is exceeded and to activate the circuitry to drain charge from the lens, thereby darkening the lens. Conversely, the low reference voltage is used to determine when too little light is passing through the lens and to activate the voltage supply used to increase the charge across the lens adjusting the lens to more transparency until the preset transmitted light level is again reached.

Both the high reference voltage and the low reference voltage are generated by using the initial bandgap voltage of a series of diodes because the voltage drop across diodes are consistently stable despite variations in the system voltage. In the preferred embodiment, the high reference voltage is determined by the voltage drop across diodes 126, 128, and 130 while the low reference voltage is determined by the voltage drop across diodes 132, 134, and 136. The high reference voltage and the low reference voltage are in the range of 1.401 volts and 1.219 volts, respectively. Resistor 138 is used to control the current through diodes 126, 128, and 130 while resistor 140 performs the same function with diodes 132, 134, and 136.

Comparator 122 compares the voltage developed from photo-diode 102 with the low reference voltage. The voltage developed from the photo-diode is connected to minus terminal 122m of comparator 122 while the low reference voltage is connected to plus terminal 122p of comparator 122. When the voltage developed from photo-diode 102 falls below the low reference voltage comparator 122 is turned on and output 122o of comparator 122 becomes system voltage 90. Transistor 142 is used to switch output 122o of comparator 122 and provide a stable SHUTDOWN signal 96. SHUTDOWN signal 96 is used to turn on the high voltage power supply, shown in FIG. 7, charging the lens structure of FIG. 4.

Charging the lens structure makes the lens more transparent resulting in photo-diode 102 sensing more light and thereby developing a greater current resulting in a greater voltage across op-amps 106 and 110. When the light sensed by photo-diode 102 is within the proper range the voltage developed by photo-diode 102 in conjunction with op-amps 106 and 110 is above the low reference voltage resulting in SHUTDOWN signal 96 being pulled to system voltage, thereby causing the high voltage power supply to be turned off. Resistor 146 is a pulldown resistor for the comparator and used to control the voltage at the base of transistor 142, while resistor 148 is used to pull SHUTDOWN signal 96 to system voltage 90 until grounded by transistor 142, turning on the high voltage power supply.

Comparator 124 of window comparator circuit 120, compares the voltage developed from photo-diode 102 with the high reference voltage. The voltage resulting from photo-diode 102 current is again connected to minus terminal 124m of comparator 124 while the high reference voltage is connected to plus terminal 124p of comparator 124. When the voltage from photo-diode 102 rises above the high reference voltage comparator 124 turns off causing CROWBAR signal 98 to be pulled to ground. CROWBAR signal 98 is used to drain charge from the lens structure thereby darkening the lens. As above, darkening the lens causes less light to be received by photo-diode 102 resulting in the voltage developed by photo-diode 102 and op-amps 106 and 108 to be lowered. When the light passing through the lens and received by photo-diode 102 returns to the desired range, the voltage developed by photo-diode 102 falls below the high reference voltage causing comparator 124 to turn on and CROWBAR signal 98 to be pulled to system voltage 90. When CROWBAR signal 98 is high no charge is drained from the lens structure and its transmissivity remains in the desired range.

Comparators 150 and op-amp 152 are used to ensure that the lens structure cannot be charged past a preset maximum safe voltage which in the preferred embodiment is 500 volts. A voltage signal proportional to the lens voltage is sent to control circuit 100 via connector 153. The development of the voltage signal will be discussed in the description of FIG. 7. The voltage signal is fed to op-amp 152 which is configured as a voltage follower. The output of op-amp 152 is connected to comparator 150 through capacitor 154 and resistor 155 which provide a time delay, if so desired, between the output of op-amp 152 and the input of comparator 150 dependant on the resulting RC constant.

The voltage received from the high voltage power supply is compared to the high reference voltage by comparator 150. When the voltage received from the high voltage power supply is equivalent to a lens voltage of the preset maximum safe voltage comparator 150 output turns off, or is pulled to ground. This in turn causes the low reference voltage to become grounded ensuring that the voltage developed from photo-diode 102 is greater than the low reference voltage. As discussed above, when the voltage developed from the photo-diode is greater than the low reference voltage, comparator 122 is off or 0 volts and the output of transistor 142, which is SHUTDOWN signal 96, is system voltage 90 causing the high voltage power supply to be turned off. In this way, whenever the voltage across the lens is at or above the preset maximum safe voltage comparator 152 forces SHUTDOWN signal 96 to turn off the high voltage power supply.

Figure 7:
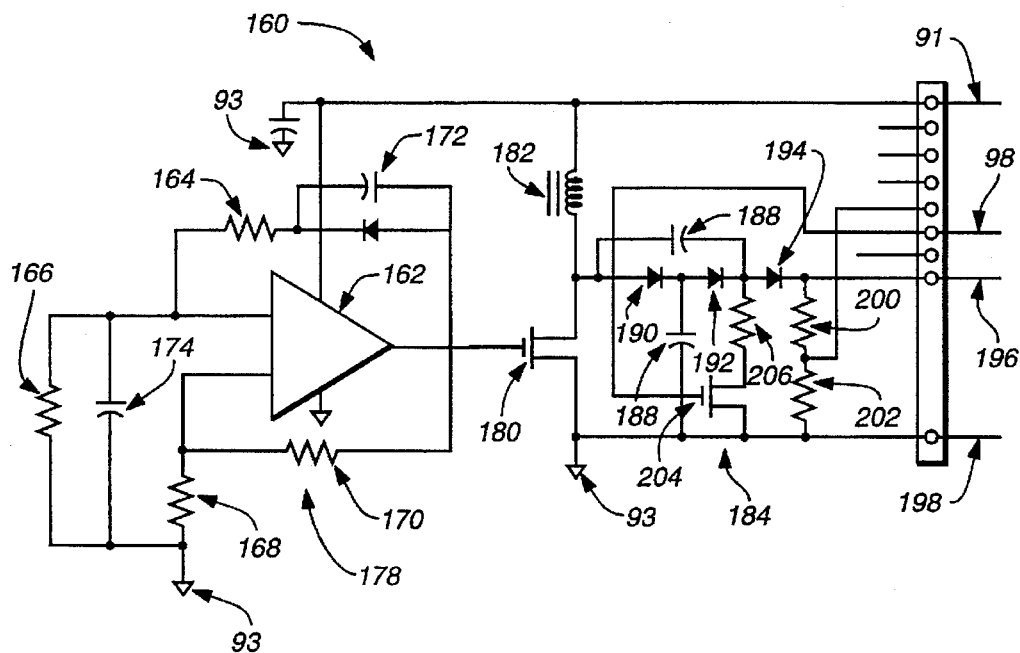
FIG. 7 is a schematic diagram of the preferred embodiment of the high voltage power supply.

FIG. 7 is a circuit diagram of high voltage power supply 160, the preferred embodiment of the high voltage power supply of the present invention. High voltage power supply 160 can also be referred to as a boost switching power supply. High voltage power supply 160 begins with op-amp 162 which together with resistors 164, 166, 168 and 170 and capacitors 172 and 174 form pulse generator 178. Pulse generator 178 produces an pulse output determined by the time constant formed by resistor 164 and capacitor 174. The output of op-amp 162 which is also the output of pulse generator 178 is connected to the base of switching transistor 180. Switching transistor 180 is used to control inductor 182.

Figure 9:
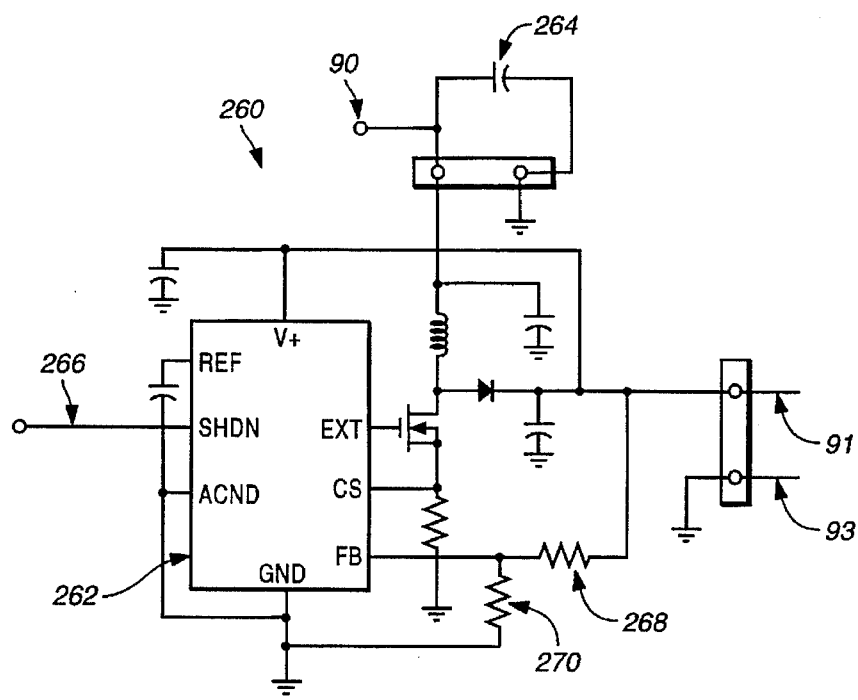
FIG. 9 is a schematic diagram of the preferred embodiment of the low voltage power supply.

Switching transistor 180 when turned on by square wave generator 178 connects inductor 182 between positive power 91 and negative power 93, both developed by the low voltage power supply shown in FIG. 9, allowing inductor 182 to charge. When pulse generator 178 switches its output, switching transistor 180 is turned off and inductor 182 is no longer connected to negative power 93, but instead discharges the energy stored during the charging phase into capacitors 186 and 188. Capacitors 186 and 188 are prevented from discharging by diodes 190, and 192, and build up charge each time inductor 182 discharges causing the voltage across the capacitors to increase with each charging phase.

This charge forms a voltage across high voltage terminals 196 and 198, across which the lens structure is connected. The resulting voltage across 196 and 198 is the sum of the voltage across capacitors 186 and 188. For example, if the voltage built up across capacitors 186 and 188 is 250 volts for each capacitor the voltage seen across high voltage terminals 196 and 198 and therefore the lens structure is 500 volts.

Resistors 200 and 202 form a voltage divider in parallel with high voltage terminals 196 and 198. The voltage drop across resistor 202 is proportional to the voltage across the lens structure and forms the feedback voltage sent from the high voltage power supply to control circuit 100 of FIG. 6 through connector 153.

Transistor 204 and resistor 206 form the mechanism by which charge is drained primarily from the PLZT lens, thereby reducing the voltage across the high voltage terminals. Base 204b of transistor 204 is connected to CROWBAR signal 98 from control circuit 100 of FIG. 6. When CROWBAR signal 98 is at system voltage 90, transistor 204 is turned on and provides a connection between capacitors 186 and 188 and ground allowing capacitors 186 and 188 to discharge until CROWBAR signal 98 is switched from system voltage 90 to ground.

Figure 8:
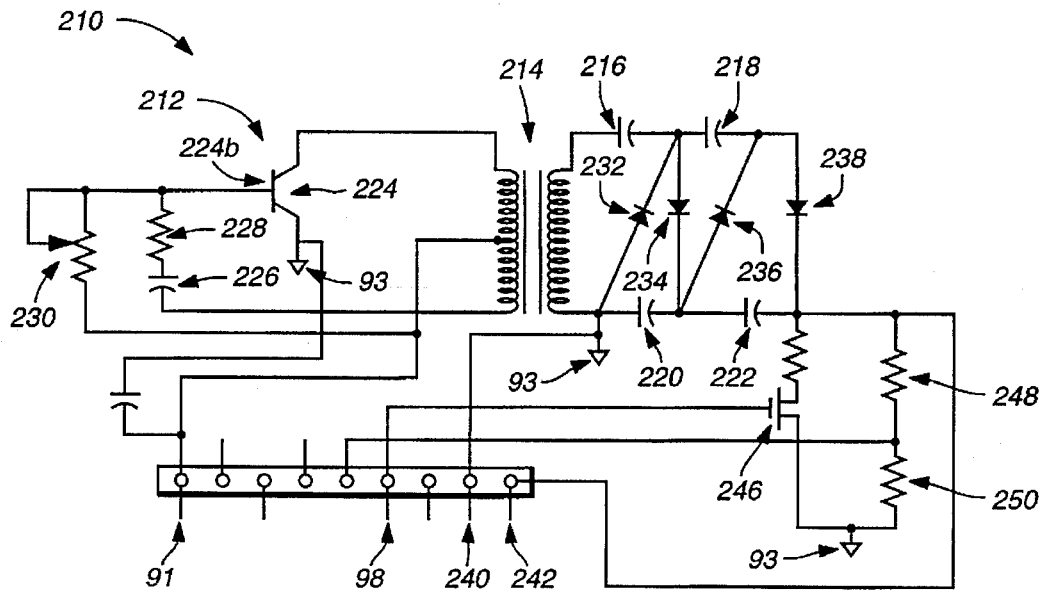
FIG. 8 is a schematic diagram of an alternate embodiment of the high voltage power supply.

FIG. 8 is a circuit diagram of a circuit implementing an alternate embodiment of the high voltage power supply. Alternate high voltage power supply 210 utilizes a self-oscillating transformer circuit 212 to charge capacitors 216, 218, 220, and 222. Self-oscillating transformer circuit 212 is formed by transformer 214 which is controlled by transistor 224. Transistor 224 has its base 224b connected to feedback capacitor 226, feedback resistor 228, and variable resistor 230 which are used to control the switching of transistor 224 and the output of self-oscillating transformer circuit 212 by the setting of the value of variable resistor 230.

Self-oscillating transformer circuit 212 charges capacitors 216 and 218 when current flows through transformer 214 in one direction and charges capacitors 220 and 222 when current flows through transformer 214 in the opposite direction. Capacitors 216, 218, 220, and 222 are prevented from discharging by diodes 232, 234, 236, and 238 and, therefore, build-up voltage in the same manner as described above in the preferred high voltage power supply of FIG. 7. High voltage terminals 240 and 242 are connected to electrical connection 60 and 62 of the lens structure shown in FIG. 5 and represent the sum of voltages across all four capacitors 216, 218, 220, and 222. The use of four capacitors requires that each only need charge to a value of 125 volts in order for 500 volts to appear at high voltage terminals 240 and 242. The disadvantage of this circuit is that transformer 224 is quite large, whereas inductor 182 of FIG. 7 is comparatively small, on the order of 0.1 inches in diameter.

CROWBAR signal 98 utilizes transistor 246 to drain charge from the lens structure, by turning on transistor 246 and providing a path for capacitors 216, 218, 220, and 222 to discharge whenever CROWBAR signal 98 is made high, or system voltage 90 by control circuit 100 shown in FIG. 6. Additionally, resistors 248 and 250 form a voltage divider in parallel with high voltage terminals 240 and 242. The voltage drop across resistor 250 is proportional to the voltage across the lens structure and forms the feedback voltage sent from the high voltage power supply to control circuit 100 of FIG. 6 through connector 153.

FIG. 9 is a circuit diagram of the preferred embodiment of the low voltage power supply. Low voltage power supply 260 is used to provide system voltage 90 as well as positive power 90 and negative power 92 which are used to power the high voltage power supply of either FIG. 7 or FIG. 8. Low voltage power supply uses voltage regulator 262, which is preferably a Maxim MAX772 voltage regulator, to regulate the voltage provided by lithium 264 and supply a stable positive power 91 and negative power 93. System voltage 90 is drawn directly from lithium cell 264 so that control circuit 100 is always powered. ON/OFF input 266 of voltage regulator 262 is connected to SHUTDOWN signal 96 from control circuit 100 of FIG. 6. This connection allows control circuit 100 to connect and disconnect power to the high voltage power supply by turning on and off voltage regulator 262. By this manner, SHUTDOWN signal 96 is used to activate the high voltage power supply to charge the lens structure as described with reference to FIG. 6.

Low voltage power supply 260 can be used without a high voltage power supply to provide the required voltage in a dichroic dye lens structure as described with reference to FIG. 1. The dichroic dye lens structure only requires in the range of 18 volts maximum. This level of voltage can be developed using only voltage regulator 260. The voltage at positive power 91 and negative power 93 is controlled by resistor $R_x$ 268 and $R_y$ 270 according to the relationship $V=((R_x-R_y)/R_y)1.5$. With positive power 91 and negative power 93 terminals connected across the lens structure, control circuit 100 of FIG. 6 can be used with low voltage power supply 260 to control the transmissivity of eyewear 10 from FIG. 1.

The preferred embodiment of control circuit 100 shown in FIG. 6 utilizes the following parts and component values:

| Drawing No. | Type | Part No. | Manufacturer |
|---|---|---|---|
| 142 | Transistor | ZRA1250FOCT | Zetech |
| 122, 124, 150 | Comparator | LP339 | Natl.Semiconductor |
| 152 | Op-Amp | LP324 | Natl.Semiconductor |
| 125, 130, 134, 136 | Diode | BAU99 | Zetech |
| 126, 132 | Diode | IN914 | |

The preferred embodiment of high voltage power supply circuit 160 shown in FIG. 7 utilizes the following parts and component values:

| Drawing No. | Type | Part No. | Manufacturer |
|---|---|---|---|
| 162 | Op-Amp | Max 474 | Maxim |
| 180, 204 | Transistor | MTD2N50E | Motorola |
| 182 | Inductor | 78F102J | J. W. Miller |
| 190, 192 | Diode | IN4927 | |
| 194 | Diode | IN914 | |

The preferred embodiment of high voltage power supply circuit 210 shown in FIG. 8 utilizes the following parts and component values:

| Drawing No. | Type | Part No. | Manufacturer |
|---|---|---|---|
| 214 | Transformer | F073 | Micro Trans |
| 224 | Transistor | FMMT5551 | Zetech |
| 244 | Transistor | ZRA1250 | Zetech |
| 246 | Transistor | MTD1N60E | Motorola |
| 232, 234, 236, 278 | Diode | IN4937 | |

The above listed parts and components can be obtained from various electrical parts manufacturers. Specifically, general components and Zetech, Plessey and Phillips parts can be obtained from Digi-Key Corp., Thief River Falls, Minn. National Semiconductor components can be obtained from National Semiconductor, Santa Clara, Calif. J. W. Miller component can be obtained from the J. W. Miller Division of Bell Industries, Gardens, Calif. Maxim components can be obtained from Maxim Integrated Products, Sunnyvale, Calif. Motorola components can be obtained from Motorola, Inc., Schaumburg, Ill. The MicroTrans transistor can be obtained from MicroTrans, Inc., Valley Stream, N.Y., and the PLZT lenses can be obtained from Aura Systems, Inc., El Segundo, Calif. Finally, the lithium cell is preferably a Tadiran TL5134 3.6 V cell available from Newark Electronics, Chicago, Ill.

While the invention has been particularly shown and described with reference to a preferred embodiment, it will be understood by those skilled in the art that various changes in form and detail may be made therein without departing from the spirit and scope of the invention.

What is claimed is:

1. An optical device to be worn by a user comprising:
   a) a lens structure having an optical transmissivity which is electrically controllable, the lens structure including a pair of lenses having a transmission layer therebetween, the transmission layer being responsive to a variable voltage applied thereto for varying an amount of light transmitted through the lens structure;
   b) a frame coupled to the lens structure, wherein the frame places the lens structure in optical relationship with the user's eyes;
   c) a sensor mounted behind the lens structure to measure the amount of transmitted light passing through the lens structure; and
   d) a control circuit electrically coupled to the lens structure and the sensor, and including a power source, the control circuit sensing and responding to the amount of light transmitted through the lens structure as measured by the sensor and electronically adjusting the optical transmissivity of the lens structure by varying the variable voltage applied to the transmission layer such that the amount of light transmitted through the lens remains within a predetermined range.

2. The optical device of claim 1 further comprising a second lens structure, the frame being configured to place the lens structure and the second lens structure in relationship to the user's respective eyes.

3. The optical device of claim 1 wherein the transmission layer is a ferro-electric material and the pair of lenses are each polarizing lenses.

4. The optical device of claim 1 wherein the ferro-electric material is composed of a lead-lanthanum zirconate/titanate (PLZT).

5. The optical device of claim 1 wherein the transmission layer is a dichroic dye sealed between the pair of lenses.

6. An optical device for controlling an amount of light received at a wearer's eye, the optical device comprising:
   a) a frame;
   b) a lens structure mounted in the frame, the lens structure including;
      i) a first lens;
      ii) a second lens;
      iii) a transmission layer disposed between the first lens and the second lens, the transmission layer having a electro-optic property in response to and in proportion to an electric field placed across the transmission layer such that the transmission layer determines the amount of light that passes through the lens structure; and
      iv) electrical terminals electrically connected across the transmission layer to produce an electric field across the transmission layer;
   c) a sensor mounted behind the second lens to develop a signal proportional to the light passing through the lens structure;
   d) a control circuit electrically connected to the sensor, the control circuit comparing the signal to a maximum transmission level and a minimum transmission level to ensure that the light passing through the lens structure is within a desired range; and
   e) a power supply electrically connected to the electrical terminals and controlled by the control circuit, the power supply used to add and remove charge from the lens structure in response to the control circuit.

7. The optical device of claim 6 wherein the first lens and the second lens are polarizing lenses, the first lens used to polarized incident light into a transmission plane, and wherein the transmission layer is a ferro-electric material which continuously rotates the transmission plane in an amount proportional to the electric field such that a percentage of the transmission plane is absorbed by the second lens, the percentage corresponding to the amount of rotation.

8. The optical device of claim 7 wherein the power supply is a high voltage power supply capable of placing a voltage across the electrical terminals of at least 500 volts.

9. The optical device of claim 7 wherein the ferro-electric material is composed of a lead-lanthanum zirconate/titanate (PLZT).

10. The optical device of claim 6 wherein the transmission layer is a dichroic dye sealed between the first lens and the second lens, the dichroic dye increasing transmissivity in response to the electric field.

11. The optical device of claim 6 wherein the control circuit and the power supply are mounted in the frame.

12. An optical device for controlling an amount of light received at a wearer's eye, the optical device comprising:
   a) a frame;
   b) a lens structure mounted in the frame, the lens structure including;
      i) a first polarizer having a first plane of polarization to receive light incident on the optical device and to transmit polarized light, the polarized light being polarized in the first plane of polarization;
      ii) a transmission layer adjacent the first polarizer to receive the polarized light, the transmission layer having an electro-optic property such that the transmission layer rotates the polarized light in response to and in an amount proportional to an electrical field placed across the transmission layer;
      iii) a second polarizer adjacent the transmission layer opposite the first polarizer and having a second plane of polarization, the second polarizer to receive the polarized light rotated by the transmission layer and to transmit a percentage of the polarized light, the percentage corresponding to the amount of rotation and the second plane of polarization; and
      iv) electrical terminals connected to the transmission layer, the electrical terminals capable of holding a charge, the charge inducing the electric field across the transmission layer;
   c) a sensor mounted on the second lens opposite the transmission layer, the sensor generating a signal proportional to the percentage of polarized light transmitted by the second polarizer;
   d) a high voltage power supply and electrically connected to the electrical terminals, the high voltage power supply used to control the charge on the electrical terminals by placing a voltage across the electrical terminals, wherein the voltage is continuously variable up to a maximum safe voltage; and
   e) a control circuit and electrically connected to the sensor and the high voltage power supply, the control circuit receiving the signal from the sensor and causing the high voltage power supply to add or remove charge as necessary when the signal from the sensor is outside a desired operating range.

13. The optical device of claim 12 wherein the transmission layer material is composed of a lead-lanthanum zirconate/titanate (PLZT).

14. The optical device of claim 12 wherein the first plane of polarization and the second plane of polarization are in an identical orientation such that the lens structure is transparent when the electric field across the transmission layer is zero.

15. The optical device of claim 12 wherein the first plane of polarization is perpendicular to the second plane of polarization such that the lens structure is opaque when the electric field across the transmission layer is zero.

16. The optical device of claim 12 wherein the frame includes a seal extending from the frame to a forehead of the wearer and a first and second earpieces, the seal and the first and second earpieces providing a barrier to prevent ambient light from reaching the sensor.

17. The optical device of claim 12 wherein the sensor is a photoamperic sensor configured to generate a current when exposed to a light source.

18. The optical device of claim 17 wherein the photoamperic sensor is a gallium arsenide phosphide light emitting diode which generates the current in response to light in essentially a visible spectrum.

19. The optical device of claim 12 wherein the high voltage power supply and the control circuit are mounted in the frame.

20. An optical device for maintaining a preset transmission level of light at a wearer's eye, the eyewear apparatus comprising:
   a) a frame including a left earpiece and a right earpiece and a seal, the left earpiece, the right earpiece and the seal preventing light from reaching the wearer's eye other than through the eyewear apparatus;
   b) a lens structure mounted in the frame and including a first and second lens, each of the first and second lenses formed by
      i) a first polarizer mounted in frame and having a first plane of polarization, wherein the first polarizer receives ambient light and transmits polarized light;
      ii) a lead-lanthanum zirconate/titanate (PLZT) layer mounted in the frame adjacent the first polarizer, the (PLZT) layer including a plurality of filaments such that an electric field is developed across the (PLZT) layer when a voltage is applied to the plurality of filaments, wherein the (PLZT) layer receives the polarized light, rotates the polarized light in an amount proportional to the electric field, and transmits rotated polarized light;
      iii) a second polarizer mounted in the frame adjacent to the (PLZT) layer opposite the first polarizer, the second polarizer having a second plane of polarization, wherein the second polarizer receives the rotated polarized light from the (PLZT) layer and transmits the preset light level to the wearer's eye; and
      iv) electrical terminals electrically connected to the plurality of filaments;
   c) a sensor mounted on the second polarizer of the first lens, wherein the sensor develops a signal proportional to the preset light level transmitted by the second polarizer of the first lens;
   d) a high voltage power supply mounted in the frame and electrically connected to the electrical terminals, wherein the high voltage power supply supplies a continuously variable voltage to the electrical terminals and a maximum safe voltage of at least 500 volts;
   e) a control circuit mounted in the frame, the control circuit being electrically connected to the sensor and the high voltage power supply, wherein the control circuit causes the high voltage power supply to alter the continuously variable voltage across the electrical terminals in response to the signal from the sensor corresponding to the preset light level having strayed outside a preset transmission range.

21. The optical device of claim 20 wherein the first plane of polarization and the second plane of polarization are in an identical orientation such that the lens structure is transparent when the electric field across the transmission layer is zero.

22. The optical device of claim 20 wherein the first plane of polarization is perpendicular to the second plane of polarization such that the lens structure is opaque when the electric field across the transmission layer is zero.

23. The optical device of claim 20 wherein the sensor is a light emitting diode configured to generate a current when exposed to a light source.

24. The optical device of claim 20 wherein the light emitting diode is a Gallium Arsenide Phosphide diode which generates the current in response to light in essentially a visible spectrum.

* * * * *